United States Patent [19]

Wagner et al.

[11] 4,051,165

[45] Sept. 27, 1977

[54] PREPARATION OF BIURET POLYISOCYANATES

[75] Inventors: Kuno Wagner, Leverkusen; Kurt Klinkmann, Hitdorf, both of Germany

[73] Assignee: Bayer Aktiengesellschaft, Leverkusen, Germany

[21] Appl. No.: 47,134

[22] Filed: June 17, 1970

[30] Foreign Application Priority Data

June 19, 1969 Germany .............................. 1931055

[51] Int. Cl.$^2$ .......................................... C07C 119/042
[52] U.S. Cl. ........................ 260/453 AB; 260/2.5 AT; 260/77.5 AT
[58] Field of Search ................. 260/453 AB, 77.5 AC

[56] References Cited

U.S. PATENT DOCUMENTS

| 2,842,506 | 7/1958 | Roussel | 260/77.5 X |
| 2,973,361 | 2/1961 | Rudner | 260/77.5 X |
| 3,239,480 | 3/1966 | Windemuth et al. | 260/77.5 X |
| 3,358,010 | 12/1967 | Britain | 260/453 |

OTHER PUBLICATIONS

"Kirk–Othmer Encyclopedia of Chemical Technology," Second Edition, vol. 12, Interscience Publishers, Inc., New York, NY 1967, pp. 45, 48–50.

*Primary Examiner*—Dolph H. Torrence
*Attorney, Agent, or Firm*—Gene Harsh; Lawrence S. Pope

[57] ABSTRACT

A method of preparing biuret polyisocyanates by reacting diisocyanates with up to about 0.4 mol per mol of diisocyanate of a monohydric tertiary alcohol in the presence of from about 0.001 to about 0.1 mol per mol of tertiary alcohol of a catalyst consisting of salts and salt mixtures of nitrogen containing bases and organic or inorganic acids at a temperature of between about 60° and about 210° C. The volume/time yield of biuret polyisocyanate according to this process is from 3 to 5 times greater than volume/time yields obtained with comparative known methods.

10 Claims, No Drawings

PREPARATION OF BIURET POLYISOCYANATES

This invention relates to an improvement in the method of preparing biuret polyisocyanate and more particularly to an improvement in the method of preparing biuret polyisocyanates from diisocyanates and monohydric tertiary alcohols.

Polyisocyanates having a biuret structure are known in the art and are widely used particularly in the form of aliphatically substituted biuret polyisocyanates as precursors in the production of polyurethane resins which are light fast and as lacquer coatings which have maximum light fastness, a high resistance to chalking and which retain a good gloss. Polyisocyanates having a biuret structure may be obtained by reacting any polyisocyante with water, compounds which split-off water, tertiary alcohols, such as, for example tertiary butanol, $H_2S$, formic acid or by hydrogenating polyaddition products of polynitriles or nitro compounds in the presence of polyisocyanates. Their formation proceeds via the intermediate stage of a urea diisocyanate to which additional diisocyanate becomes attached via the hydrogen atoms of the urea groups. If tertiary butanol is used as a reactant, for example in the process described in U.S. Pat. No. 3,358,010, it has the disadvantage in that relatively high temperatures of from 180° C. to 205° C. are necessary for the reaction to proceed sufficiently rapid. If, when carrying out the reaction on a production scale, reaction temperatures of about from 195° C. to 200° C. are maintained with a view to obtaining high volume/time yields, the insufficient resistance of the reaction mixtures to discoloration at elevated temperatures often gives rise to discolored, brownish polyisocyanates. Furthermore, the resistance of the biuret polyisocyanates to discoloration at elevated temperatures prepared by the process according to U. S. Pat. No. 3,358,010, optionally in the presence of acid compounds, such as, hydrochloric acid or sulphuric acid as catalysts, is severely reduced.

It is therefore an object of this invention to provide a method of preparing biuret polyisocyanates devoid of the foregoing disadvantages. It is a further object of this invention to provide biuret polyisocyanates having superior physical properties. Another object of this invention is to provide a method of preparing biuret polyisocyanates having improved colorfastness. Yet another object of this invention is to provide a method of preparing biuret polyisocyanates in which the volume/time yield is from 3 to 5 times greater than that of known methods.

The foregoing objects and others are accomplished according to the invention, generally speaking, by reacting diisocyanates with up to about 0.4 mol of a monohydric tertiary alcohol per mol of diisocyanate in the presence of from about 0.001 to 0.1 mol per mol of tertiary alcohol of a catalyst consisting of salts or salt mixtures of nitrogen containing bases and organic or inorganic acids at a temperature of from about 60° to about 210° C. The catalyzed reaction between diisocyanates and tertiary alcohol is preferably carried out in the presence of isocyanate containing addition products of any isocyanate with hydrazine or hydrazine derivatives.

The great increase in the volume/time yields obtained by the use of the catalysts and catalyst mixtures accordingto the invention is particularly surprising in the preparation of aliphatic, cycloaliphatic and araliphatic biuret polyisocyanates. Examples 1, 2 and 4 illustrate the great increase in reaction velocity obtained by the use of the catalysts according to the invention compared with with the reaction velocity found when carrying out the uncatalyzed preparation of biuret isocyanates in accordance with the process described in U.S. Pat. No. 3,358,010.

The process according to the invention thus leads to particularly desirous volume/time yields from an industrial point of view, for the formation of biuret polyisocyanates. As is evident from from Example 1, this amounts to from about 600 to 640 g/l per hour, whereas the volume/time yield in uncatalyzed reactions is only about 126 g/l per hour. The new process thus provides almost a 5-fold increase in the volume/time yield in the preparation of biuret polyisocyanates.

A comparison of the two sets of data given in Table 1 shows also the considerable advantage of the more rapid decomposition of tertiary butyl urethanes in the end phase of the reaction, since, in the uncatalyzed preparation of biuret polyisocyante, approximately from 10 to 12% of the tertiary butyl urethanes decompose extremely slowly, as can be illustrated by preparing a plot of $\%Co_2$ vs. reaction time of the comparative data given in Table 1. The process according to the invention therefore, in addition provides for optimum utilization of the teritary alcohol used in the reaction, and accordingly leads to increased yields of biuret polyisocyanates with increased NCO content.

Some catalysts suitable for use according to the process of the invention are, for example, hydrohalic acid salts, preferably hydrochlorides of ammonia; primary, secondary, tertiary, aliphatic, cycloaliphatic, araliphatic, aromatic and heterocyclic bases, such as, for example ammonium choloride, methylammonium cholride, dimethylammonium chloride, trimethylammonium chloride, ethylammonium chloride, diethylammonium chloride, propylammonium chloride, n-butylammonium chloride, di-n-butylammonium chloride, stearyl-methylammonium chloride, morpholine piperazine, N-aminomorpholine, N-amino-N-methyl-piperazine, N,N'-diaminopiperazine and carbazic esters or carboxylic acid hydrazide derivatives of the above-mentioned hydrazines. Furthermore, any hydrazinium salts of the above-mentioned compounds with phosphoric acid, phosphorous acid, chloroacetic acid, trichloroacetic acid, oxalic acid and formic acid are suitable catalysts.

Particularly preferred catalysts for use in the invention are diethylammonium chloride, dimethylammonium chloride, N,N'-dimethylhydrazinium chloride, triethylammonium chloride and dimethylbenzylammonium chloride.

Mixtures of the above-mentioned catalysts are also suitable, such as, for example dimethylammonium chloride and N,N'-dimethylhydrazinium chloride (1:1); diethylammonium chloride and N,N'-dimethylhydrazinium chloride (1:1); triethylammonium chloride and N,N'-dimethylhydrazinium chloride (1:2); diethylammonium chloride and N,N'-diethylhydrazinium chloride (1:2); mixtures of diethylammonium chloride, N,N'-dimethylhydraziniium chloride and N,N'-dimethylammonium formate and the like.

The above-mentioned catalysts or catalyst mixtures may be added in the solid or liquid form to the mixtures of polyisocyanate and tertiary butanol at normal or elevated temperature, but they may also be added in solution, particularly in carbamic acid chlorides which are hydrolyzed in moist air. When partially hydrolyzed carbamic acid chlorides are used, the use of aminohydrochlorides may be dispensed with since aminohydrochlorides are formed by the hydrolysis of the corresponding carbamic acid chlorides. Some particularly preferred carbamic acid chlorides are, for examples, N,N'-dimethylcarbamic acid chloride, N,N'-diethylcarbamic acid chloride, N-methylethylcarbamic acid chloride, N,N'-di-N-butylcarbamic acid chloride, N-methylcarbamic acid chloride, N-ethylcarbamic acid chloride, N-cyclohexylcarbamic acid chloride, N-benzylcarbamic acid chloride or N-phenylcarbamic acid chloride.

Hydrolyzed addition products of phosgene and chloroformic acid esters with tertiary organic bases which contain, as products of hydrolysis, the catalytically active hydrochlorides of the corresponding organic bases, are also suitable. Acetyl chloride, benzyl chloride, propionic acid chloride, benzoyl chloride, benzotrichloride, trichloromethylisocyanide dichloride, bis-chloromethylcarbamic acid chloride and the methyl and ethyl esters of chloroformic acid and dimethyl sulphate may also be used to advantage in small quantities as satisfactory solvents for the catalysts or for catalyst mixtures according to the invention.

The catalysts or catalyst mixtures according to the invention are advantageously used in amount of from about 0.001 to about 0.1 mol, preferably of from about 0.009 to about 0.005 mol, per mol of tertiary alcohols used. It is immaterial whether they are added to the tertiary alcohol, to the diisocyanate or to the mixture of tertiary alcohol and polyisocyanate. Since, for example, mixtures of any polyisocyanates with the quantities of tertiary butanol commonly used for the preparation of biuret are miscible at room temperature without evolution of heat, and the reactions proceed at a measurable rate only above 70° C., the additions of catalyst do not reduce the stability of such mixtures when stored in, for example, tanks or reservoirs.

One variation of the process according to the invention which is particularly preferred consists of including, as co-catalysts to the aforementioned catalysts and catalyst mixtures, semicarbazide polyisocyanates which contain —NCO groups or carbamic acid chloride groups which co-catalysts can be prepared by the method desscribed, for example, in Belgian patent specification No. 721,031. This results in an additional increase in the reaction velocity of the process according to the invention and, furthermore, an increased resistance of the reaction mixtures and of the isolated biuret polyisocyanates to discoloration at elevated temperatures when they are employed industrially in the production of, for example, light-gas lacquers, coatings of foam plastics.

When carrying out the reaction according to the invention, such hydrazino isocyanates or their hydrochlorides and carbamic acid chlorides may be added to the reaction mixtures as the isolated materials, but they may also be prepared in situ by adding small quantities of hydrazine, methylhydrazine, ethylhydrazine and particularly N,N'-dimethylhydrazine, to the reaction mixtures before or after the addition of the catalysts according to the invention, which then react with the excess polyisocyanate to yield polyisocyanates which contan semicarbazide groups. These pefreferred heat stabilizers and co-catalysts are advantageously used in amounts of from 0.023 to 0.3 mol and preferably of from 0.04 to 0.2 mol, based on the amount of diisocyanate used, in the preparation of biuret polyisocyanates. It is immaterial whether they are added to the tertiary butanol, to the polyisocyante or to the resulting mixture of polyisocyanate and teritiary butanol.

The teritiary alcohols mentioned in U.S. Pat. No. 3,358,010, such as, for example, tertiary butyl alcohol, 2-methyl-2-butanol, 2-methyl-2-pentanol, 3-methyl-3-pentanol, 3-ethyl-3-pentanol, 1-methylcyclopentanol, 1-methylcyclohexanol, 1-ethylcyclohexanol and 1, 1-dimethylallyl alcohol are suitable for carrying out the process according to the invention. The peferred alcohol is tertiary butyl alcohol.

Some aliphastic, cycloaliphatic and araliphatic diisocyanates which are suitable for use as starting materials for the process according to the invention are, for example, tetramethylene diisocyanate, pentamethylene diisocyanate, hexamethylene diisocynte, 1,3-cyclopentylene diisocyanate, 1,4-cyclohexylene diisocyanate, 1,2-cyclohexylene diisocyanate, hexahydroxylylene diisocyanate, 4,4'-dicyclohexyl diisocyanate, 1,2-di-(isocyanatomethyl)-cyclobutane, 1,3-bis-(isocyanatopropoxy)-2,2-dimethylpropane, 1,3-bis-(isocyanatopropyl)-2-methyl-2-propylpropane, 1-methyl-2,4-diisocyanatocyclohexane, 1-methyl-2,6-diisocyanatocyclohexane, bis-(4-isocyanatocyclohexyl)-methane, 1,4-diisocyanatocyclohexane and 1,3-diisocyanatocyclohexane, m- and p-xylylene diisocyanate, isophorone diisocyanate and 2,6-diisocyanatocaproic acid ester.

Particularly preferred aliphatic, cycloaliphatic and araliphatic diisocyanates are hexamethylene diisocyanate, the isomeric mixture of 1-methyl-2,4-diisocyanatocyclohexane and 1-methyl-2,6-diisocyanatocyclohexane, bis-(4-isocyanatocyclohexyl)-methane, m- and p-xylene diisocyanate, isophorone diisocyanate, methyl-substituted hexamethylene- and pentamethylene diisocyanate and 2,6-diisocyanatocaproic acid ester.

Aromatic diisocyanates suitable for use in the invention are, for example, 1-methylbenzene-2,4-diisocyanate, 1-methylbenzene-2,6-diisocyanate, the commercial toluylene diisocyanate mixtures, m- and p- phenylene diisocyanate, naphthylene diisocyanate, diphenylmethane diisocyanates, di- and triisopropylbenzene diisocyanates, 1-(isocyanatophenyl)-ethylisocyanate, and diisocyanates which have been substituted by various substitutents, such as alkoxy-, nitro- chloro- or bromo-substituted diisocyanates. Addition products of diisocyanates with subequivalent quantities of dihydroxy compounds such as butanediol or neopentyl glycol are also suitable for the preparation of modified types of biuret. Mixtures of various polyisocyanates may also be used for the formation of biuret. Diphenylmethane diisocyanates which contain carbodiimide groups are also very suitable for biuret formation, particularly those which can be prepared accoding to German patent specification No. 1,092,007. Also suitable are diisocyanates which contain semicarbazide groups prepared according to Belgian patent specification No. 721,031 from asymmetrically disubstituted hydrazines, which constitute excellent antoxidants, color stabilizers at elevated temperatures and age resistors.

Methylbenzene-2,4-diisocyanate, 1-methylbenzene-2,6-diisocyanate and commercial mixtures of isomers, such as, for example mixtures of 65 to 80 parts by weight of 1-methylbenzene-2,4-diisocyanate and 35 to 20 parts by weight of 1-methylbenzene-2,6-diisocyanate, and 4,4'-diisocyanatophenylmethane may be mentioned as examples of aromatic diisocyanates which are very suitable for biuret formation.

In the process according to the invention, at least about 2.5 mols of a diisocyanate are reacted with 1 mol of tertiary alcohol, however, optimum results are obtained by reacting from about 6 to about 10 mols of diisocyanate with 1 mol of teritary alcohol. When using a very large excess of diisocyanate, it may be desirable to remove unreacted diisocyanate from the biuret polyisocyanate formed, by distillation or extraction. When distillation is employed it is advisable to use a thin layer evaporator or a rotary evaporator. When preparing polyurethane resins from solutions of biuret polyisocyanates in monomeric diisocyanates, it is of course, unnecessary to remove the excess of diisocyanate.

The formation of biuret polyisocyanate generally proceeds via the formation of a unsaturated hydrocarbon, evolution of carbon dioxide and the intermdiate stage of a urea diisocyanate from which the polyisocyanate with biuret structure is then formed by reacting with additional diisocyanate. The progress of the reaction may be determined by monitoring the amount of carbon dioxide evolved.

The temperature for the reaction according to the invention must lie between about 60° C. to about 210° C., a temperature range of from about 150° C. to about 190° C. being particularly preferred. The resulting polyisocyanates with biuret structure have the theoretical formula:

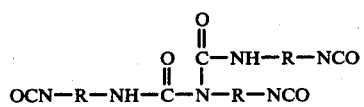

in which R represents an aliphatic, cycloaliphatic, araliphatic or aromatic radical which is obtained by removing the isocyanate groups from the abovementioned diisocyanates. If the temperature of 190° C. is exceeded, excess diisocyanate may react with the hydrogen atoms of the biuret structure to form higher fuctional isocyanates, which may in some cases be desired.

The reaction is generally carried out in the absence of solvents, but may be carried out in the presence of inert solvents, such as, for example dioxane, tetrahydrofuran, triethylene glycol, diacetate, toluene, benzene, chlorobenzene-o-di-chlorobenzene, butyl acetate ethylene glycol monoethyl ether acetate and the like.

Biuret polyisocyanate mixtures are generally solid or resinous substances or more or less viscous oils at room temperature. They are surprisingly high soluble in monomeric liquid or molten di- and polyisocyanates, such as, for example toluylene diisocyanates or multinuclear polyisocyanates, such as, 4,4'-diisocyanatodiphenylmethane, its commercial isomeric mixtures, liquid modification products which contain carbodiimide groups, dicyclohexylmethane-4,4'-diisocyanate, diphenyldimethylemethane-4,4'-diisocyanate and 4,6-dimethyl-1,3-xylylene diisocyanate. The biuret polyisocyanates are also very compatible and miscible with many different isocyanate-containing addition products of diisocyanates with low molcular weight diols and triols, such as, glycol, trimethylol propane and glycerol and with polymerized low molecular weight polyisocyanates which may contain several isocyanurate rings in the molecule.

The preferred polyisocyanates which are based on hexamethylene diisocyanate, toluylene diisocyanates or 4,4'-diisocyanatodiphenylmethane, are prepared so as to constitute from about 45 to about 50% biuret polyisocyanate solutions in monomeric diisocyanates, are transparent mixtures which are stable in storage and which have a viscosity of between about 30 and about 400 centipoises measured at about 21° C. Their mixtures with liquid commercial polyisocyanates, which are obtained for example, for phosgenation of aniline-formaldehyde condensates, also have a relatively low viscosity. Where from 65 to 70% solutions are used, the viscosities are found to be from about 1400 to about 200 centipoises measured at about 21° C.

The biuret polyisocyanates of the invention are useful as valuable starting materials in the production and modification of synthetic resins by the polyisocyanate polyaddition process and are particularly suitable for the production of light fast lacquer coatings, foam resins, elastomers, coatings and impregnations. These biuret polyisocyanates may also be used for the production of semi-rigid polyurethane resins which have been foamed in the mold and which have a compact surface and cellular core in which smooth, homogeneous and heat resistant outer zones and cellular cores are obtained.

The invention is further illustrated, but it is not intended that it be limited, by the following examples in which all parts and percentages are by weight unless otherwise specified.

EXAMPLE 1

About 37 parts of tertiary butyl alcohol are mixed with about 504 parts by weight of hexamethylene diisocyante. About 2.5 parts by weight of N,N-dimethylhydrazine are added dropwise with rapid stirring. The following mixtures are prepared by adding to proportionate quantities of the above mixture, the following:

a. About 1.12 parts of dimethylammonium chloride,
b. About 1.2 parts of N,N-dimethylhydrazinium chloride,
c. About 1.52 parts of diethylammonium chloride,
d. About 2.28 parts of di-n-butylammonium chloride,
e. About 3.2 parts of dimethylbenzylammonium chloride,
f. About 1.8 parts of morpholine hydrochloride,
g. About 1.9 parts of piperidine hydrochloride.

Each of the reaction mixtures (a) to (g) is adjusted to a reaction temperature of about 185° C. and the amount of carbon dioxide and isobutylene liberated is determined by means of a gas meter. In all the experiments (a) to (g), liberation of gas and formation of biuret polyisocyanate are terminated after from about 40 to about 50 minutes and the course of reactionis as indicated by the data given in Table 1, Column A. For purposes for comparison the uncatalyzed reaction data is given in Column B of Table 1. The solutions of biuret polyisocyanate in monomeric hexamethylene diisocyanate obtained have the following NCO values and viscosities:

| | |
|---|---|
| (a) 36.7% NCO | 34 centipoise/21° C. |
| (b) 37.1% NCO | 33 centipoise/21° C. |
| (c) 36.3% NCO | 35 centipoise/21° C. |
| (d) 36.9% NCO | 34 centipoise/21° C. |
| (e) 37.2% NCO | 32 centipoise/21° C. |
| (f) 36.8% NCO | 34 centipoise/21° C. |
| (g) 37.4% NCO | 33 centipoise/21° C. |

If in experiments (a) to (g) excess hexamethylene diisocyanate is removed in a thin layer evaporator at about 130° C. and about 0.2 mm Hg., practically colorless biuret polyisocyanates which have a high resistance to discoloration at elevated temperatures (NCO content from 20.5 to 21.5%) are obtained in yields of from 238 to 242 parts by weight. If the biuret polyisocyanate prepared in experiment (a) is stoved with a polyester polyol of phthalic acid anahydride and trimethylol propane with an OH content of about 8.5% at a temperature of about 230° C. for a few seconds so as to produce a highly cross-linked lacquer film, the film obtained is completely colorless, whereas as lacquer film which has been produced in a similar manner from biuret polyisocyanates which have been prepared using HCl or $H_2SO_4$ as catalysts or by uncatalyzed reaction, are discolored dark brown to reddish.

EXAMPLE 2

Exactly the same procedure is employed as in Example 1 but the catalyst used is a mixture of about 0.3 parts of dimethylammonium chloride, about 0.5 parts of N,N-dimethylhydrazinium chloride and about 1.5 parts of dimethylcarbamic acid chloride and the reaction is carried out at a temperature of about 165° C.

Here again the decomposition of tertiary butyl urethane, which is represented by the data given in Table 2, Column A is found to be greatly accelerated compared with that in the uncatalyzed comparison sample, which is given in Table 2, Column B and again a biuret polyisocyanate of high resistance to discoloration at elevated temperatures is obtained. When stoved with polyhydroxyl compounds, this biuret polyisocyanate gives rise to practically colorless lacquers of maximum light fastness and gloss retention.

Stoving lacquers which contain the biuret polyisocyanate prepared by the process according to the invention as a binder and which have been stoved at about 230° C. are colorless, whereas those lacquers which contain biuret polyisocyanate which has been prepared without a catalyst have a brown to reddish tinge after stoving.

EXAMPLE 3

The same procedure as in Example 2 is employed, but the following polyisocyanates and catalyst mixtures are used for about 37 parts of tertiary butyl alcohol:

a. About 666 parts of isophorone diisocyanate, about 1.8 parts of triethylammonium chloride and about 1 part of ethylhydrazinium chloride.

The speed of the reaction is determined by the quantity of $CO_2$ and isobutylene evolved. The following reaction times are found, based on approximately 96% conversion to biuret polyisocyanates:

| Experiment | Reaction time at 165° in minutes; Catalysts according to the invention | Uncatalyzed Reaction |
| --- | --- | --- |
| a | 184 | 375 |
| b | 175 | 375 |
| c | 169 | 345 |
| d | 180 | 345 |
| e | 190 | 360 |
| f | 185 | 360 |
| g | 182 | 364 |
| h | 168 | 360 |
| i | 165 | 360 |

EXAMPLE 4

The same procedure as described in Example 1 (a) is employed but the reaction is carried out at about 140° C. and the diisocyanate used is about 522 parts by weight of commercial toluylene diisocyanate consisting of about 80% of 1-methyl-benzene-2,4-diisocyanate and about 20% of 1-methylbenzene-2,6-diisocyanate. The catalyst is used in a mixture of about 1.2 parts of dimethylammonium chloride and about 3 parts of the carbamic acid chloride of about 3 mols of hydrogen chloride and about 1 mol of the diisocyanate of about 1 mol of N,N-dimethylhydrazine and about 2 mols of hexamethylene diisocyanate.

An approximately 50% solution of biuret polyisocyanates having an NCO value of about 37.1% and a viscosity of about 123 centipoises measured at about 20° C. is obtained. The polyisocyanate mixture is transparent, has an elevated resistance to discoloration at elevated temperatures and has less tendency to discoloration in the core in the case of production of foams than comparable biuret polyisocyanates prepared without a catalyst. The acceleration of the formation of biuret polyisocyanate is illustrated by the date given in Table 3, Column A representing the catalyzed reaction and Column B the uncatalyzed reaction.

If a plot of $\%CO_2$ vs. reaction time is prepared the slow uncatalyzed decomposition of tertiary butyl urethanes in the end phase of the uncatalyzed reaction is demonstrably evident.

EXAMPLE 5

The procedure described in Example 4 is employed, but the reaction is carried out at about 160° C. and about 750 parts of 4,4'-diisocyanatodiphenylmethane, about 72 parts of a polyisocyanate of about 1 mol of N,N-dimethylhydrazine and about 2 mols of hexamethylene diisocyanate, and about 2 parts of dimethylcarbamic acid chloride containing about 0.8 parts of dimethylamine hydrochloride are used. The following reduced reaction times in the catalyzed reaction are found at approximately 96% conversion to biuret polyisocyanates:

| Experiment | Reaction time in minutes at 160° C. and 95% conversion |
| --- | --- |
| According to Example 5 | 95 |
| uncatalyzed | 150 |

The approximately 50% biuret polyisocyanate solutions obtained have a substantially higher resistance to discoloration at elevated temperatures and less tendency to yellowing than the comparison sample prepared without catalyst. Polyurethane foams and polyurethane elastomers prepared from them have increased light fastness and resistance to discoloration at elevated temperatures.

Although, the invention has been illustrated in considerable detail in the foregoing example, it is to be understood that one skilled in the art may make many variations without departing from the spirit and scope of the invention.

TABLE 1

Formation of Biuret Polyisocyanate from Hexamethylene Diisocyanate and Tertiary Butanol at About 185° C., According to Example 1

| Reaction Time, Minutes | A $\%CO_2{}^1$ in catalyzed reaction | B $\%CO_2{}^1$ in uncatalyzed reaction |
| --- | --- | --- |
| 0 | 0 | 0 |
| 15 | 50 | 25 |
| 30 | 80 | 40 |
| 45 | 95 | 55 |
| 60 | 100 | 60 |

TABLE 1-continued

Formation of Biuret Polyisocyanate from Hexamethylene Diisocyanate and Tertiary Butanol at About 185° C., According to Example 1

| Reaction Time, Minutes | A %CO$_2$[1] in catalyzed reaction | B %CO$_2$[1] in uncatalyzed reaction |
|---|---|---|
| 120 | — | 85 |
| 180 | — | 90 |
| 240 | — | 95 |

[1]%CO$_2$ = decomposition of tertiary butanol = % of biuret polyisocyanate formation At about 96% conversion, the following volume/time yields are determined for the biuret polyisocyanate formation A. Catalyzed Reaction according to the invention: about 600 to 640 grams per liter per hour
B. Uncatalyzed Reaction: about 126 grams per liter per hour.

TABLE 2

Formation of Biuret Polyisocyanate from Hexamethylene Diisocyanate and Tertiary Butanol at 165° C., According to Example 2.

| Reaction Time Minutes | A %CO$_2$[1] in catalyzed reaction | B %CO$_2$[1] in uncatalyzed reaction |
|---|---|---|
| 0 | 0 | 0 |
| 15 | 20 | 8 |
| 30 | 40 | 17 |
| 45 | 55 | 25 |
| 60 | 65 | 30 |
| 120 | 90 | 50 |
| 180 | 100 | 60 |
| 240 | — | 70 |
| 300 | — | 75 |
| 360 | — | 80 |

[1]%CO$_2$ = % decomposition of tertiary butanol = % of biuret formation.

TABLE 3

Formation of Biuret Polyisocyanates from Toluylene Diisocyanates and Tertiary Butanol at about 140° C., According to Example 4.

| Reaction Time Minutes | A %CO$_2$[1] in catalyzed reaction | B %CO$_2$[1] in uncatalyzed reaction |
|---|---|---|
| 0 | 0 | 0 |
| 15 | 20 | 8 |
| 30 | 30 | 15 |
| 45 | 45 | 20 |
| 60 | 50 | 25 |
| 120 | 75 | 45 |
| 180 | 90 | 60 |
| 240 | 95 | 80 |
| 300 | — | 85 |
| 360 | — | 90 |

[1]%CO$_2$ = % decomposition of tertiary butanol = % of Biuret formation

What is claimed is:

1. A process for the preparation of biuret polyisocyanates which comprises reacting at a temperature of from about 60° C to about 210° C diisocyanates and up to about 0.4 mol per mol of diisocyanate of a tertiary alcohol selected from the group consisting of tertiary butyl alcohol, 2-methyl-2-butanol, 2-methyl-2-pentanol, 3-methyl-3-pentanol, 3-ethyl-3-pentanol, 1-methyl cyclo-pentanol, 1-methylcyclohexanol, 1-ethylcyclohexanol and 1,1-dimethylallyl alcohol in the presence of from about 0.001 to about 0.1 mol per mol of tertiary alcohol of a catalyst selected from the group consisting of hydrochlorides of ammonia and aliphatic, cycloaliphatic, araliphatic, aromatic and heterocyclic nitrogen containing bases wherein the nitrogen atoms of said bases are primary secondary or tertiary.

2. The process of claim 1 wherein the reaction is carried out in the presence of from about 0.023 to 0.3 mol per mol of diisocyanate of an —NCO containing addition product consisting of about 2 mols of a monomeric diisocyanate and 1 mol of N, N-dimethylhydrazine.

3. The process of claim 1 wherein the diisocyanate is hexamethylene diisocyanate.

4. The process of claim 1 wherein the tertiary alcohol is tertiary butyl alcohol.

5. The process of claim 1 wherein the catalyst is added in the form of a solution in liquid carbamic acid chlorides or polycarbamic acid chlorides.

6. The process of claim 1 wherein the reaction mixture is heated at a temperature of about 185° C. for about 0.5 to about 1 hour.

7. A process for the preparation of biuret polyisocyanates which comprises reacting at a temperature of from about 60° to about 210° C diisocyanates and up to about 0.4 mol per mol of diisocyanate of a tertiary alcohol selected from the group consisting of tertiary butyl alcohol, 2-methyl-2-butanol, 2-methyl-2-pentanol, 3-methyl-3-pentanol, 3-ethyl-3-pentanol, 1-methyl cyclopentanol, 1-methylcyclohexanol, 1-ethylcyclohexanol and 1,1-dimethylallyl alcohol in the presence of from about 0.001 to about 0.1 mol per mol of tertiary alcohol of a catalyst selected from the group consisting of ammonium chloride and hydrochloride acid salts containing between 1 and 8 carbon atoms derived from nitrogen containing aliphatic, cycloaliphatic, araliphatic, aromatic or heterocyclic bases and wherein the nitrogen atoms of said bases are primary, secondary, or tertiary.

8. A process for the preparation of biuret polyisocyanates which comprises reacting at a temperature of from about 60° C to about 210° C diisocyanates and up to about 0.4 mol per mol of diisocyanate of a tertiary alcohol selected from the group consisting of tertiary butyl alcohol, 2-methyl-2-butanol, 2-methyl-2-pentanol, 3-methyl-3-pentanol, 3-ethyl-3-pentanol, 1-methyl cyclopentanol, 1-methylcyclohexanol, 1-ethylcyclohexanol and 1,1-dimethylallyl alcohol in the presence of from about 0.001 to about 0.1 mol per mol of tertiary alcohol of a catalyst wherein the catalyst is a mixture of N,N-dimethylhydrazine hydrochloride and dimethylamino hydrochloride.

9. A process for the preparation of biuret polyisocyanates which comprises reacting at a temperature of from about 60° C. to about 210° C. diisocyanates and up to about 0.4 mol per mol of diisocyanate of a tertiary alcohol selected from the group consisting of tertiary butyl alcohol, 2-methyl-2-butanol, 2-methyl-2-pentanol, 3-methyl-3-pentanol, 3-ethyl-3-pentanol, 1-methyl cyclopentanol, 1-methylcyclohexanol, 1-ethylcyclohexanol and 1,1-dimethylallyl alcohol in the presence of from about 0.001 to about 0.1 mol per mol of tertiary alcohol of a catalyst consisting of ammonium chloride, methylammonium chloride, dimethylammonium chloride, trimethylammonium chloride, ethylammonium chloride, diethylammonium chloride, propylammonium chloride, n-butylammonium chloride, di-n-butylammonium chloride, stearyl-methylammonium chloride, dimethylbenzylammonium chloride, and the hydrochloride salts of morpholine, piperazine, N-aminomorpholine, N-amino-N-methylpiperazine and N,N'-diaminopiperazine and mixtures of these catalysts.

10. The process of claim 9 wherein the catalyst is selected from the group consisting of diethylammonium chloride, dimethylammonium chloride, N,N'-dimethylhydrazinium chloride, triethylammonium chloride, dimethylbenzylammonium chloride and mixtures of these catalysts.

* * * * *